US012389521B2

(12) United States Patent
Yanovitz et al.

(10) Patent No.: US 12,389,521 B2
(45) Date of Patent: *Aug. 12, 2025

(54) PLASMA GENERATING SYSTEM

(71) Applicant: CAPS Medical Ltd., Netanya (IL)

(72) Inventors: Leonid Yanovitz, Rishon LeZion (IL);
Ilan Oleg Uchitel, Kfar-Saba (IL);
Boris Kogan, Kiriat-Motzkin (IL)

(73) Assignee: CAPS Medical Ltd., Netanya (IL)

( * ) Notice: Subject to any disclaimer, the term of this patent is extended or adjusted under 35 U.S.C. 154(b) by 287 days.

This patent is subject to a terminal disclaimer.

(21) Appl. No.: 18/130,163

(22) Filed: Apr. 3, 2023

(65) Prior Publication Data

US 2024/0023224 A1    Jan. 18, 2024

Related U.S. Application Data

(63) Continuation-in-part of application No. 17/866,700, filed on Jul. 18, 2022, now Pat. No. 11,627,652.

(51) Int. Cl.
*H05H 1/46* (2006.01)
*A61N 1/40* (2006.01)
*H01F 27/28* (2006.01)

(52) U.S. Cl.
CPC ............ *H05H 1/4652* (2021.05); *A61N 1/40* (2013.01); *H01F 27/28* (2013.01); *H05H 2245/32* (2021.05)

(58) Field of Classification Search
None
See application file for complete search history.

(56) References Cited

U.S. PATENT DOCUMENTS 4,956,582 A   9/1990  Bourassa
5,909,086 A   6/1999  Kim et al.
(Continued)

FOREIGN PATENT DOCUMENTS

CN   103377869   10/2013
EP   3773288     2/2021
(Continued)

OTHER PUBLICATIONS

European Search Report and the European Search Opinion Dated Sep. 13, 2024 From the European Patent Office Re. Application No. 24167544.6. (7 Pages).
(Continued)

*Primary Examiner* — Srinivas Sathiraju

(57) ABSTRACT

Power circuitry for cold plasma generation; optionally plasma for therapeutic use. Cold plasma generation occurs at the distal end of a catheter-like device which is flexible, narrow (e.g., less than 5 mm in diameter), and longitudinally extended to reach, e.g., 50-100 cm into body cavities. A cable used for power transmission is a part of the power generating circuit, its intrinsic impedance being a major contributor to and constraint on the time constant of an entraining RC circuit whose resonant frequency entrains the frequency of power generation. In some embodiments, inductive transformer coupling to the entraining/transmission line circuit is used to generate voltage gain. In some embodiments, transformer coupling is divided into a plurality of stages. This potentially enables practically achieving high transmission frequencies with higher gain, lowered sensitivity to variability in distal portions of the entraining RC circuit, and/or longer transmission lines compared to a single-stage transformer configuration.

21 Claims, 9 Drawing Sheets

(56) References Cited

U.S. PATENT DOCUMENTS

| | | | | |
|---|---|---|---|---|
| 6,321,531 | B1* | 11/2001 | Caren | C10L 1/1233 |
| | | | | 204/173 |
| 6,326,584 | B1* | 12/2001 | Jewett | H01J 37/32174 |
| | | | | 219/121.57 |
| 6,565,558 | B1 | 5/2003 | Lindenmeier et al. | |
| 10,692,704 | B2* | 6/2020 | Louis | B01J 19/1887 |
| 11,166,762 | B2* | 11/2021 | Eckert | A61B 18/18 |
| 11,621,587 | B1 | 4/2023 | Yanovitz | |
| 11,627,652 | B1* | 4/2023 | Yanovitz | H05H 1/4652 |
| | | | | 315/141 |
| 2008/0112202 | A1* | 5/2008 | Hu | H02M 7/539 |
| | | | | 363/132 |
| 2010/0052539 | A1 | 3/2010 | Choi | |
| 2010/0247403 | A1 | 9/2010 | Hancock | |
| 2012/0168081 | A1 | 7/2012 | Son | |
| 2012/0268969 | A1* | 10/2012 | Cuk | H02M 7/48 |
| | | | | 363/37 |
| 2012/0279658 | A1 | 11/2012 | Bolden, II et al. | |
| 2013/0267943 | A1* | 10/2013 | Hancock | H05B 6/806 |
| | | | | 606/33 |
| 2014/0246364 | A1* | 9/2014 | Hruska | C02F 1/78 |
| | | | | 204/554 |
| 2014/0246381 | A1* | 9/2014 | Buchanan | C01B 13/115 |
| | | | | 210/748.19 |
| 2014/0319382 | A1* | 10/2014 | Hancock | H05H 1/46 |
| | | | | 315/111.21 |
| 2015/0078053 | A1* | 3/2015 | Harrison | H02M 7/4807 |
| | | | | 363/132 |
| 2015/0097434 | A1* | 4/2015 | Harrison | H02M 7/4807 |
| | | | | 307/43 |
| 2015/0157870 | A1* | 6/2015 | Kalghatgi | H05H 1/2406 |
| | | | | 604/23 |
| 2015/0232353 | A1* | 8/2015 | Denvir | C02F 1/4608 |
| | | | | 210/150 |
| 2016/0022347 | A1 | 1/2016 | Rencher et al. | |
| 2016/0123927 | A1* | 5/2016 | Persson | G01N 27/628 |
| | | | | 315/111.21 |
| 2016/0194224 | A1* | 7/2016 | Buchanan | H02M 1/12 |
| | | | | 204/554 |
| 2016/0197564 | A1* | 7/2016 | Buchanan | C02F 1/78 |
| | | | | 363/123 |
| 2016/0233059 | A1* | 8/2016 | Hensley | H05H 1/2406 |
| 2016/0251240 | A1* | 9/2016 | Fraser | C02F 1/487 |
| | | | | 204/664 |
| 2017/0014184 | A1 | 1/2017 | Hancock et al. | |
| 2017/0246468 | A1* | 8/2017 | Kalghatgi | A61N 1/44 |
| 2017/0313603 | A1* | 11/2017 | Fraser | C02F 1/4608 |
| 2018/0358205 | A1 | 12/2018 | Long et al. | |
| 2019/0036346 | A1* | 1/2019 | Hruska | H03K 3/57 |
| 2019/0206658 | A1* | 7/2019 | Roy | H01J 37/32348 |
| 2019/0230779 | A1* | 7/2019 | Sanders | H01J 37/32174 |
| 2019/0391387 | A1* | 12/2019 | Neophytou | H01J 37/32541 |
| 2020/0254271 | A1 | 8/2020 | Eckert et al. | |
| 2020/0325049 | A1* | 10/2020 | Roy | A61L 2/24 |
| 2021/0051790 | A1* | 2/2021 | Yancey | H05B 41/16 |
| 2021/0068896 | A1* | 3/2021 | Eckert | G01R 29/0892 |
| 2021/0385933 | A1 | 12/2021 | Eckert et al. | |
| 2023/0126911 | A1 | 4/2023 | Uchitel | |
| 2023/0132232 | A1 | 4/2023 | Uchitel et al. | |
| 2024/0022116 | A1 | 1/2024 | Yanovitz et al. | |
| 2024/0023224 | A1* | 1/2024 | Yanovitz | H01F 27/28 |

FOREIGN PATENT DOCUMENTS

| | | | | |
|---|---|---|---|---|
| ES | | 2556231 | 1/2016 | |
| ES | | 2556231 T3 * | 1/2016 | A61B 18/042 |
| ES | | 2688300 | 10/2018 | |
| ES | | 2688300 T3 * | 10/2018 | A61B 18/042 |
| KR | 10-2022-0028774 | | 3/2022 | |
| PL | | 222184 | 7/2016 | |
| WO | WO 2004/014439 | | 2/2004 | |
| WO | WO 2022/098245 | | 5/2022 | |
| WO | WO 2024/018464 | | 1/2024 | |
| WO | WO 2024/018465 | | 1/2024 | |

OTHER PUBLICATIONS

International Search Report and the Written Opinion Dated Nov. 13, 2023 From the International Searching Authority Re. Application No. PCT/IL2023/050755 (13 Pages).

International Preliminary Report on Patentability Dated Jan. 30, 2025 From the International Bureau of WIPO Re. Application No. PCT/IL2023/050755 (6 Pages).

Notice of Allowance Dated Mar. 13, 2024 from the US Patent and Trademark Office Re. Application No. 18/129,116. (12 pages).

International Search Report and the Written Opinion Dated Nov. 8, 2023 From the International Searching Authority Re. Application No. PCT/IL2023/050754 (10 Pages).

Official Action Dated Oct. 30, 2023 from US Patent and Trademark Office Re. U.S. Appl. No. 18/129,116. (17 pages).

Notice of Allowance Dated Jan. 19, 2023 from the US Patent and Trademark Office Re. U.S. Appl. No. 17/866,700. (6 pages).

Notice of Allowance Dated Jan. 19, 2023 from the US Patent and Trademark Office Re. U.S. Appl. No. 17/971,737. (14 pages).

Official Action Dated Sep. 26, 2022 from US Patent and Trademark Office Re. U.S. Appl. No. 17/866,700. (15 pages).

Ayachit et al. "Transfer Functions of a Transformer at Different Values of Coupling Coefficient", IET Circuits and Devices Systems, 10(4): 337-348, Jul. 1, 2016.

* cited by examiner

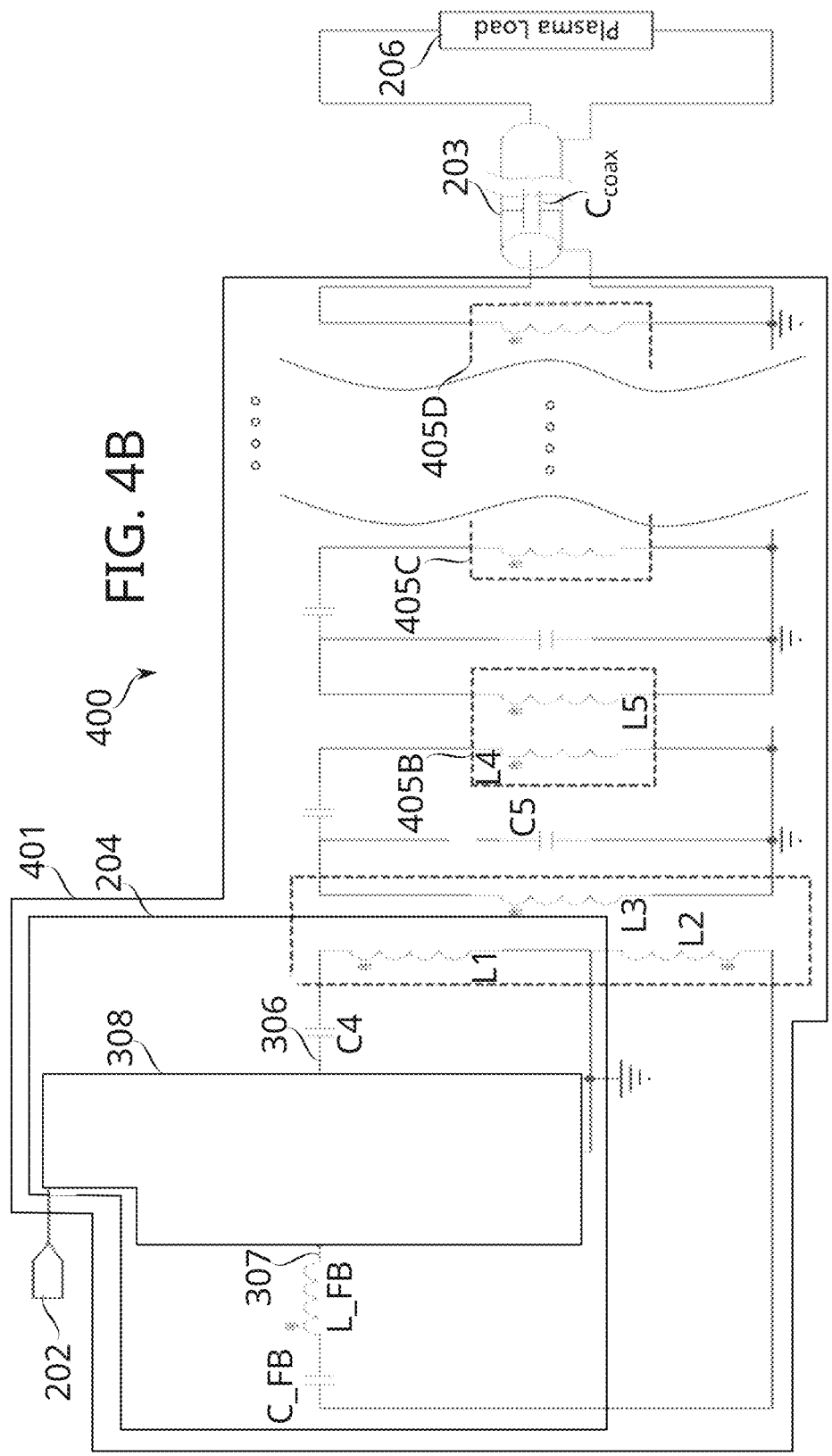

PLASMA GENERATING SYSTEM

RELATED APPLICATION

This application is a Continuation-in-Part (CIP) of U.S. patent application Ser. No. 17/866,700 filed on Jul. 18, 2022, the contents of which are incorporated herein by reference in their entirety.

FIELD AND BACKGROUND OF THE INVENTION

The present invention, in some embodiments thereof, relates to the field of plasma generation, and more particularly, but not exclusively, to generation and therapeutic delivery of cold plasma.

Non-Thermal Atmospheric Plasma (NTAP), also referred to as Cold Atmospheric Plasma (CAP), is a near room-temperature ionized gas composed of various neutral and charged species. It is widely used in various application fields and industries, including in medicine where its beneficial characteristics are well established. Application of NTAP on tissue exerts complex and unique impact both on cell/tissue level and systemic level.

NTAP may be generated by Dielectric Barrier Discharge (DBD), wherein a flowing gas (typically, a noble gas such as Helium or Argon) is ionized by an electrode upon which high voltage is periodically applied. the electrode is covered by a dielectric barrier, such that no direct ohmic path is generated between the driving source and the applied target tissue.

SUMMARY OF THE INVENTION

According to an aspect of some embodiments of the present disclosure, there is provided power supply circuitry for a non-thermal plasma generator, the circuitry including: a gain transformer including a primary coil and a secondary coil; a driver circuit electrically connected to drive a current through the primary coil; a load circuit having a distal end including a plasma generating site, and a proximal end coupled to the secondary coil of the gain transformer; wherein the load circuit includes at least one decoupling transformer inductively interconnecting the plasma generating site and the secondary coil.

According to some embodiments of the present disclosure, the load circuit has an impedance determining a frequency of its oscillation in response to current generated in the secondary coil.

According to some embodiments of the present disclosure, the load circuit entrains oscillation of the driver circuit.

According to some embodiments of the present disclosure, the load circuit oscillation is entrained via feedback from the gain transformer.

According to some embodiments of the present disclosure, the frequency of oscillation of the load circuit is sufficiently high that plasma generation at the plasma generating site does not extinguish during at least a full oscillation cycle.

According to some embodiments of the present disclosure, the gain transformer provides a gain of at least 20.

According to some embodiments of the present disclosure, the at least one decoupling transformer provides in aggregate a gain no larger than 1.

According to some embodiments of the present disclosure, the at least one decoupling transformer provides in aggregate a gain smaller than the gain provided by the gain transformer by a factor of at least 2.

According to some embodiments of the present disclosure, the gain transformer and at least one coupling transformer comprise air or ferrite cores.

According to some embodiments of the present disclosure, the at least one decoupling transformer includes a plurality of decoupling transformers.

According to some embodiments of the present disclosure, the gain transformer and at least one coupling transformer isolate the plasma generating site from ground.

According to some embodiments of the present disclosure, the load circuit includes: a transmission line, and a distal transformer of the at least one decoupling transformers including a secondary coil of the distal transformer inductively interconnected with a primary coil of the distal transformer and connected to a proximal side of the transmission line; the driver circuit: is electrically interconnected with the proximal side of the transmission line via the primary and secondary coils of the distal transformer, and provides to the transmission line an electrical signal with an operating frequency of between 1-10 MHz, which transmits to a distal end of the transmission line with an operating amplitude of at least 0.5 kV RMS; and wherein impedance on the secondary coil of the distal transformer is small enough in combination with the capacitance of the transmission line that a circuit portion including the transmission line and secondary coil operates in resonance upon receiving the electrical signal.

According to some embodiments of the present disclosure, the driver circuit ceases production of the electrical signal when the transmission line is disconnected, but maintains production of the electrical signal for values of transmission line capacitance varying within a range having at least a 10% difference between its minimum and maximum values.

According to some embodiments of the present disclosure, the operating amplitude is at least 1 kV RMS.

According to some embodiments of the present disclosure, the transmission line is at least 50 cm long, and flexible.

According to some embodiments of the present disclosure, the load circuit provides a feedback signal to the driver circuit via a feedback network.

According to some embodiments of the present disclosure, oscillation of the load circuit entrains the driver circuit, via the feedback network, to produce the electrical signal at the operating frequency.

According to some embodiments of the present disclosure, provided together with a gas supply lumen leading along the transmission line to the plasma generating site, the gas supply lumen and transmission line together being elements of a flexible probe has an overall diameter of less than 10 mm.

According to some embodiments of the present disclosure, the plasma generating site generates non-thermal plasma when powered by the electrical signal.

According to some embodiments of the present disclosure, the at least one decoupling transformer together with the gain transformer comprise a plurality of transformers interconnecting the proximal end of the transmission line to a low voltage signal oscillating at the operating frequency, with a voltage amplitude at least 20 times smaller than the operating amplitude.

According to some embodiments of the present disclosure, the primary coil of the gain transformer has an inductance in the range of about 1-5 pH, and the secondary winding of the gain transformer an inductance in the range of about 1000-5000 PH.

According to some embodiments of the present disclosure, the gain transformer includes a feedback winding providing a feedback signal to the driver circuit via a feedback network, and wherein the feedback winding has an inductance in the range of about 1-10 µH.

According to some embodiments of the present disclosure, the feedback signal entrains oscillation of the driver circuit to the operating frequency, and is received at the feedback winding via the load circuit at a frequency of electrical oscillation of the transmission line.

According to some embodiments of the present disclosure, the secondary winding of the distal transformer has an inductance in the range of about 20-80 µH, and the primary winding of the distal transformer has an inductance in the range of about 5-20 PH.

According to some embodiments of the present disclosure, the secondary winding of the distal transformer is connected to conductors of the transmission line through electrical contacts.

According to some embodiments of the present disclosure, the power supply circuitry includes pulse modulation circuitry operable to modulate the operating frequency at a lower frequency including a frequency in the range of 0.1-1 KHz.

According to an aspect of some embodiments of the present disclosure, there is provided a method of decoupling gain and frequency constraints on non-thermal plasma generation, including: providing a site of plasma generation an output electrical signal having an operating frequency and a voltage amplitude sufficient to generate plasma; wherein the site of plasma generation is electrically interconnected via at least two transformer stages to an input electrical signal oscillating at the operating frequency and at least 20 time lower in voltage than the output electrical signal.

According to some embodiments of the present disclosure, the voltage amplitude is at least 1 kV.

According to some embodiments of the present disclosure, the operating frequency is between 1-10 MHz.

According to some embodiments of the present disclosure, the site of plasma generation is interconnected with the input electrical signal via a transmission line, and oscillation of a

CLAIMS circuit including the transmission line entrains oscillation of the input electrical signal. According to an aspect of some embodiments of the invention, there is provided a non-thermal plasma generator including: a gain transformer including a primary coil and a secondary coil; a driver circuit electrically connected to drive a current through the primary coil; a load circuit having a distal end including a plasma generating site generating non-thermal plasma, and a proximal end coupled to the secondary coil of the gain transformer; wherein the load circuit includes at least one decoupling inductor, providing inductance including inductance connected in parallel to the secondary coil, and inductance connected in parallel to the plasma generating site.

According to some embodiments of the invention, the load circuit has an impedance determining a frequency of oscillation of the load circuit in response to a current generated in the secondary coil.

According to some embodiments of the invention, the load circuit entrains oscillation of the driver circuit.

According to some embodiments of the invention, oscillation of the driver circuit is entrained via feedback from the gain transformer.

According to some embodiments of the invention, the frequency of oscillation of the load circuit is sufficiently high that plasma generation at the plasma generating site does not extinguish during at least a full oscillation cycle.

According to some embodiments of the invention, the non-thermal plasma generator includes pulse modulation circuitry operable to modulate the frequency of oscillation at a lower frequency within the range of 0.1-1 KHz.

According to some embodiments of the invention, the gain transformer provides a gain of at least 20.

According to some embodiments of the invention, the at least one decoupling inductor includes at least one decoupling transformer, providing in aggregate a gain no larger than 1.

According to some embodiments of the invention, the at least one decoupling inductor includes decoupling transformers providing in aggregate a gain smaller than the gain provided by the gain transformer by a factor of at least 2.

According to some embodiments of the invention, the gain transformer includes air or ferrite core.

According to some embodiments of the invention, the at least one decoupling inductor includes a plurality of decoupling transformers.

According to some embodiments of the invention, the at least one decoupling inductor includes an inductor coil connected both in parallel to the secondary coil, and in parallel to the plasma generating site.

According to some embodiments of the invention, the driver circuit ceases oscillation when the plasma generating site is disconnected from the load circuit, but maintains oscillation for values of the frequency of oscillation of the load circuit varying within a range having at least a 10% difference between minimum and maximum values of the range.

According to some embodiments of the invention, an operating voltage amplitude at the plasma generating site produced when the current is driven through the primary coil of the gain transformer is at least 1 kV RMS.

According to some embodiments of the invention, the transmission line is at least 50 cm long, and flexible.

According to some embodiments of the invention, provided together with a gas supply lumen leading along the transmission line to the plasma generating site, the gas supply lumen and transmission line together being elements of a flexible probe has an overall diameter of less than 10 mm.

According to some embodiments of the invention, the at least one decoupling inductor together with the gain transformer comprise a one or more transformers delivering the operating voltage to the plasma generating site with an amplitude at least 20 times larger than a voltage amplitude in the primary coil of the gain transformer.

According to some embodiments of the invention, the primary coil of the gain transformer has an inductance in the range of about 1-5 µH, and the secondary coil of the gain transformer has an inductance in the range of about 1000-5000 µH.

According to some embodiments of the invention, the feedback from the gain transformer is provided by a feedback winding of the gain transformer, and wherein the feedback winding has an inductance in the range of about 1-10 µH.

According to some embodiments of the invention, the at least one decoupling inductor includes at least one decoupling transformer, and a distal-side coil of the at least one decoupling transformer has an inductance in the range of about 20-80 µH, and is a coil of a distal decoupling transformer of the at least one decoupling transformer having a primary coil with an inductance in the range of about 5-20 µH.

According to some embodiments of the invention, the at least one decoupling inductor is connected to the plasma generating site through releasable electrical contacts.

Unless otherwise defined, all technical and/or scientific terms used herein have the same meaning as commonly understood by one of ordinary skill in the art to which the present disclosure pertains. Although methods and materials similar or equivalent to those described herein can be used in the practice or testing of embodiments of the present disclosure, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the present disclosure are herein described, by way of example only, with reference to the accompanying drawings. With specific reference now to the drawings in detail, it is stressed that the particulars shown are by way of example, and for purposes of illustrative discussion of embodiments of the present disclosure. In this regard, the description taken with the drawings makes apparent to those skilled in the art how embodiments of the present disclosure may be practiced.

In the drawings:

FIGS. 4A-4B schematically illustrate a resonating high-voltage plasma generating system, according to some embodiments of the present disclosure.

DESCRIPTION OF SPECIFIC EMBODIMENTS OF THE INVENTION

Figure 1A:
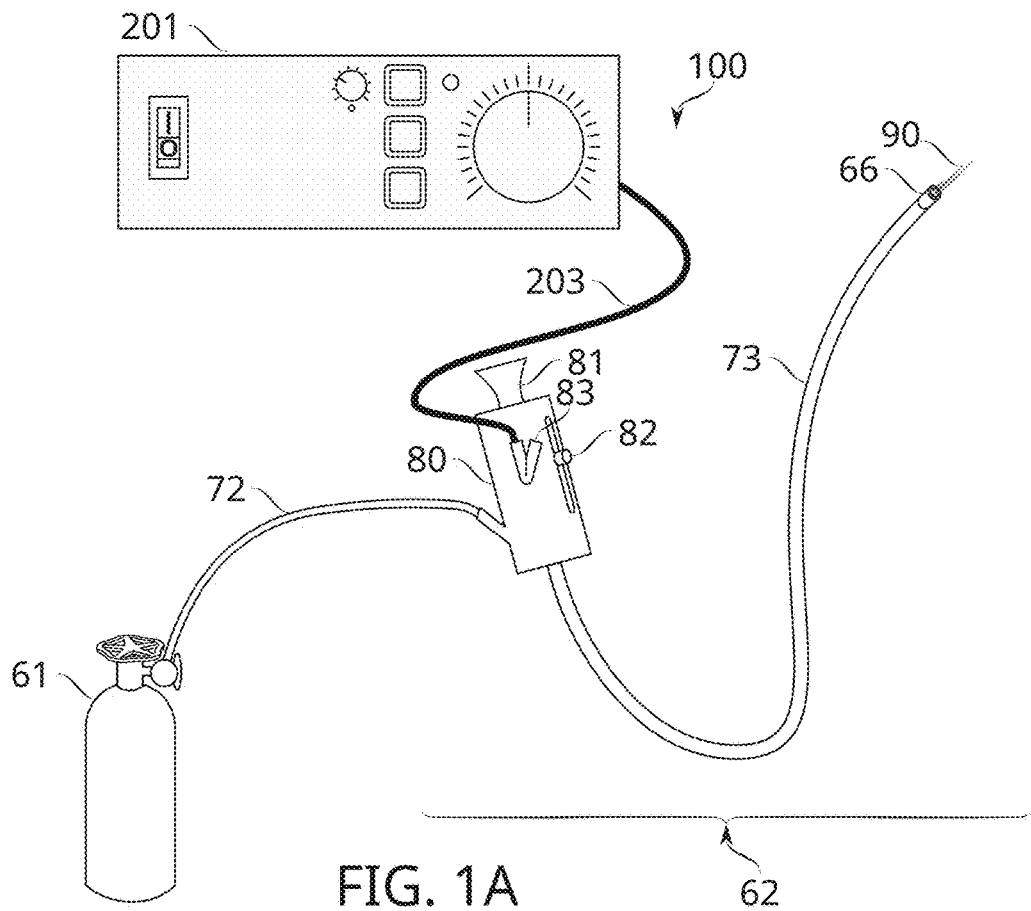
FIG. 1A schematically represents a plasma generating device, according to some embodiments of the present disclosure.

The present invention, in some embodiments thereof, relates to the field of plasma generation, and more particularly, but not exclusively, to generation and therapeutic delivery of cold plasma.

Overview

An aspect of some embodiments of the present disclosure relates to the design of electrical circuitry operable at high frequency generate power for plasma generation. In some embodiments of the present disclosure, an alternating electrical field is used to generate non-thermal atmospheric plasma (NTAP) via dielectric barrier discharge (DBD).

Alternation helps to overcome alternate "screening" effects caused by electrical charge mobility. During the positive cycle of the voltage (anode electrode), high-mobility electrons generated in the plasma are attracted to the electrode barrier. This produces an electrical screening effect leading swiftly to the plasma being extinguished. On the opposite cycle, when the electrode serves as cathode, these electrons become an ionization source to reignite the plasma-until attraction of positive ions to the cathode once again screens it. To achieve ongoing generation of plasma, the electrical field (proportional to the voltage applied to the electrode) is continuously alternated between these two cycle polarities. Although at fine temporal scales, plasma is emitted as discrete plasma bullets, the frequency of alternation is high enough that plasma output appears continuous.

There is, however, a potential consequence for efficiency, insofar as extinguished plasma generation must be re-ignited in each half-cycle. On a per-cycle basis, the energy required to maintain ignited plasma is considerably lower than the energy required to re-ignite it. On way to mitigate this is to reduce the time period during which mobile ions/electrodes move to strengthen screening—an effect which may be achieved in principle by increasing the cycle frequency. The frequency above which transient screening effects no longer cause intermittent extinguishing of plasma generation is referred to herein as the "transition frequency".

The transition frequency from bullet plasma to continuous plasma depends on the physical configuration of the system (e.g., electrode size, gas chamber dimensions, and/or electrode configuration), as well as the gas composition and environmental effects such as pressure and temperature. For a typical DBD plasma jet application, the transition frequency is typically about 1 MHz. Even at this frequency, screening effects sub-threshold for plasma extinction can still interfere with ionization efficiency. Accordingly, at still higher frequencies, power output that generates plasma may continue to increase, other parameters being equal.

As a result, tuning of the plasma generation frequency may be used as a way of controlling plasma power. For example, plasma generation frequency may be controllable within a range extending from somewhere near the device's transition frequency, up to about a factor of ten higher than that. For example, the frequency may be variable within a range from about 1 MHz up to about 10 MHz, or variable within some portion of this range.

Frequency tuning in practical electrical circuitry is subject to a variety of constraints determined and/or influenced by remaining conditions of plasma generation and performance. In some embodiments of the present disclosure, a plasma generator is operated to operate under an alternating (e.g., sinusoidal) voltage with a root mean square (RMS) value of about 0.5-2 kV (for example, 1 kV RMS).

Herein, the term "continuous plasma" refers to continuity through a single high-frequency signal cycle of 100 kHz or higher. Optionally, the term refers to a train of a plurality of such cycles. However trains of such cycles may be interrupted; for example, subjected to pulse width modulation (PWM) at a frequency in a range between about 0.1 and 1 kHz (e.g., 600 Hz). The duty cycle is optionally adjusted to any suitable percentage up to 100% (for example, 66%). In some embodiments, a plasma generating system may comprise PWM circuitry, e.g., PWM circuitry operable at least within such ranges.

Apart from characteristics particular to plasma generation, a generator's performance and efficiency strongly depend more generally on load characteristics and required bandwidth. In particular, a generator may be most efficient at a certain operating frequency of the circuit. For a plasma generator, this operating frequency may fall, for example, within the range of 1 MHz to 10 MHz; but other frequencies also within that range are potentially significantly less efficient. The operating frequency may be at or near a natural resonating frequency of the circuit. Additionally or alternatively, to support a wider range of resistive and capacitive loads, a generator's design may sacrifice efficiency and performance (e.g., frequency stability, distortion, and/or power loss).

In some embodiments of the present disclosure, a plasma generator is configured for use in medical field applications. The configuration includes, in particular, a spatial separation of a plasma generating unit from a power generation unit that drives it. The power generation unit may be too cumbersome to place near a treated organ and/or patient. In intra-body plasma applications where a plasma delivery probe is advanced into and/or through confined spaces, the electrical driving circuitry for the probe is simply too large to accompany the probe itself.

Utility of plasma generated outside of the body (comparatively near the driving circuitry) and delivered into it is potentially degraded by the short half-lifetime of the plasma products. Electrical characteristics of the plasma may prevent its transport by more than a few centimeters within the body.

Alternatively, a high-voltage signal is transmitted to a probe distal end, at which plasma is generated and from which the plasma is applied to target tissue. Signal transmission may be over a coaxial cable, allowing safe electrical signal transmission across a relatively long distance (e.g., a meter or more, for example, at least 1, 2, 3, 4 or 5 meters) while retaining power and signal integrity. The structure of coaxial line has potential advantages for miniaturization and flexibility when used in intra-body applications, e.g., in catheter-type devices which may be advanced for distances of several centimeters (e.g., 10, 50, 100 or more centimeters) beyond an opening in the body such as a natural orifice and/or a keyhole incision.

As is further described hereinbelow, use of a coaxial transmission line, though a practical solution for power transmission to a relatively remote site of plasma generation, becomes part of an interlocking system of parameters which, in some embodiments of the present disclosure, are considered constrain the transmission frequency to be near a certain resonant frequency of the transmission line (and the RC network of which it is a part) for best efficiency.

If the transmission line is part of an RC network which has a resonant frequency away from the power transmission frequency, there may be excessive losses in the transmission line itself (e.g., resulting in heating, potentially to a degree that imposes limits on operation such as reduced duty cycle), and/or inefficiencies in transmitting power into the line which increase requirements on the power supply in terms, e.g., of its size, cost, and/or robustness. At resonance, inductance and capacitance can operate to cancel each other out and reduce resistive power losses.

Effects of electrical losses which produce heating in particular are potentially more significant when transmission is over a low-diameter transmission line, e.g., due to its correspondingly reduced thermal mass. In some embodiments of the present disclosure, diameter of the transmission line (e.g., less than 5 mm, 3 mm, less than 2 mm, or less than 1.5 mm) is a constraint on the minimum diameter of body cavities which can be accessed, insofar as the transmission line is used as a portion of a probe which is advanced through the body cavity to a target of plasma delivery.

A problem arises furthermore due to the high slew rate needed to provide a high voltage signal (e.g., 0.5 kV or higher RMS) at a high frequency (e.g., 1 MHz or higher). It may be difficult to cause the transmission load to follow such a slew rate, without the use of resonance driving. Resonance drive also, in some embodiments, provides a built-in power shutoff in case of accidental disconnection of or sufficiently severe damage to the transmission line, insofar as this interrupt the generation of a feedback signal which in turn entrains the frequency of power generation.

The considerations just described result in an interlocking system of engineering constraints. Here is a brief example of how constraints can interlock, which is explained in more detail below. (1) A voltage requirement at the plasma generator may be 1 kV RMS in order to achieve plasma discharge. (2) To reach 1 kV RMS from a reasonable input-side voltage of 20-33 V, the power generator's transformer gain should be in the range of about 30-50 (optionally, larger than 20, larger than 25, or larger than 30). (3) This ratio is also proportional to the square root ratio of two inductances (primary and secondary inductances) used in a transformer that can produce this gain. (4) But the output-side inductance (the secondary inductance) is constrained to a low level by (5) the same efficiency constraint that motivates selection of a high resonant frequency for delivering power to the plasma generating probe; for example a frequency of about 2 MHz. With too high an inductance, this frequency cannot be met without drastically reducing capacitance instead—but (6) this, in some embodiments, is primarily provided by the intrinsic capacitance of the coaxial cable needed to transmit power. Finally, (7), the input-side inductance (primary inductance) is constrained to be lower still than even the secondary inductance. But this is potentially an impractically low value. This may manifest in design pressure to abandon, for example, one or more of the *desiderata* of a low input voltage, a high operating frequency, or a long power transmission line.

In some embodiments of the present disclosure, the design pressure is relieved through another solution: use of a dual transformer configuration comprising a gain transformer, and a decoupling transformer (which may itself be divided into one or more stages). The gain transformer is freed to use practically reasonable inductance values to create voltage gain by the interposition of the decoupling transformer. In effect, isolation allows the output side of the gain transformer to have a low capacitance after all. Then, since there doesn't have to be any gain on the isolation transformer (or only a relatively low gain), the primary inductance of the isolation transformer can be equal to the secondary inductance, instead of having an impractically small value forced on it by a requirement to generate voltage gain. In some embodiments, decoupling effects are produced using a same inductor coil connected in parallel with both the plasma load (distally), and another inductor coil (proximally, e.g., a secondary coil of the gain transformer). This may imitate the effect of interposing a unity gain transformer, while avoiding losses due to non-ideal inductive coupling.

As potential practical results, the introduction of an isolation stage provides a potential advantage for one or more of:

Decoupling constraints on voltage gain and on operating frequency.

Allowing increased coaxial cable length without perturbing the ability to match other design constraints.

Reducing frequency variation due to load impedance changes.

Details of these potential advantages are further described hereinbelow.

It is noted that electrical isolation from ground is provided, in some embodiments, by coupling of the site of plasma generation (which receives a high voltage) to its power through one or more ground-isolated transformers.

Before explaining at least one embodiment of the present disclosure in detail, it is to be understood that the present disclosure is not necessarily limited in its application to the details of construction and the arrangement of the components and/or methods set forth in the following description and/or illustrated in the drawings. Features described in the current disclosure, including features of the invention, are capable of other embodiments or of being practiced or carried out in various ways.

Plasma Treatment Device

Reference is now made to FIG. 1A, which schematically represents a plasma generating device 100, according to some embodiments of the present disclosure.

Plasma generating device 100, in some embodiments, comprises a high voltage power generator 201 and an ionization gas supply 61 interconnected to a plasma probe assembly 62. High voltage power generator 201 supplies ionizing voltage to plasma probe assembly 62 via cable 203 (which may be, for example, a coaxial cable, or another electrical conduit with controlled impedance). Ionizing gas supply 61 supplies an ionization gas to plasma probe assembly 62 via tubing 72. The supplied gas may comprise, for example, one or more noble gases such as neon, argon, or helium; and/or other gas(es) suitable for ionization into a plasma plume 90. Optionally, cable 203 and tubing 72 are integrated into a single cabling unit which connects with plasma probe assembly 62. Optionally, high voltage power generator 201 and ionization gas supply 61 are integrally housed.

Plasma probe assembly 62, optionally comprises a handle 80. Handle 80 is optionally provided with controls 81, 82 for controlling actuation of probe conduit 73 and/or plasma delivery tip 66, for controlling functions of power generator 201, and/or for controlling ionization gas delivery from gas supply 61. Optionally, plasma probe assembly 62 physically integrates power functions and gas delivery functions into probe conduit without use of a dedicated handle. In some embodiments, probe conduit 73 includes both a lumen for delivery of ionization gas, and a high voltage transmission line (e.g., a continuation of cable 203 and tubing 72). In some embodiments, probe conduit comprises a plurality of lumens, e.g., a lumen attached to gas supply 61 which delivers of ionization gas, and a lumen which scavenges (removes) of ionization gas, optionally under suction. In some embodiments, any one or more of the lumens of probe conduit 73 is optionally used as a working channel, by insertion of a tool. Handle 80, in some embodiments, comprises one or more ports 83 for introduction of such tools into a lumen of probe conduit 73.

In some embodiments of the present invention, probe conduit 73 and plasma delivery tip 66 are sized and otherwise configured (e.g., safety-configured) for the delivery of non-thermal plasma to an intrabody location. The intrabody location may be remotely located relative to a point of insertion, e.g., distant from a point of insertion into the body by 25 cm or more; for example, 80 cm, 100 cm, or 120 cm. Insofar as plasma tip 60 comprises the site of plasma generation (as it does in some embodiments), the device must supply ionization-level voltage (e.g., a voltage of 1 kV or more) to the tip 60. This length may place a constraint on the minimum capacitance of cable 203.

In some embodiments, probe conduit 73 (including both a lumen for delivery of ionization gas and high voltage transmission line) has an overall diameter of less than 12 mm, less than 10 mm, less than 8 mm, or less than 5 mm. The narrower the overall diameter, the narrower the minimum-sized body lumen that the probe conduit can traverse in the manner of a catheter; for example, a ureter, blood vessel, or other subcutaneous access-way to a targeted treatment site.

Figure 1B:
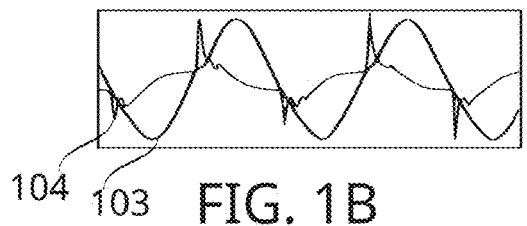
FIG. 1B is a graph of typical current-voltage waveforms of atmospheric pressure plasma at low frequency (<100 KHz), according to some embodiments of the present disclosure.
Figure 1C:
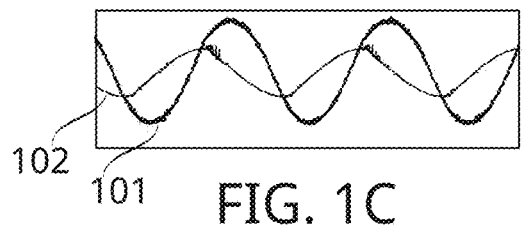
FIG. 1C graphs a typical high frequency (e.g., >1 MHz) current-voltage waveform of atmospheric pressure plasma, according to some embodiments of the present disclosure.

Reference is now made to FIG. 1B, which is a graph of typical current-voltage waveforms of atmospheric pressure plasma at low frequency (<100 KHz). Reference is also made to FIG. 1C, which graphs a typical high frequency (e.g., >1 MHz) current-voltage waveform of atmospheric pressure plasma.

While the excitation voltage 103, 101 is sinusoidal in both cases, it may be seen in FIG. 1B that the current 104 spikes as plasma bullet is ignited on each half-cycle. In the higher frequency example of FIG. 1C, the current waveform 102 more closely tracks the input voltage (with a phase shift) as continuous plasma generation maintains uniform resistance in plasma plume.

Plasma High-Voltage Generator

Figure 2A:
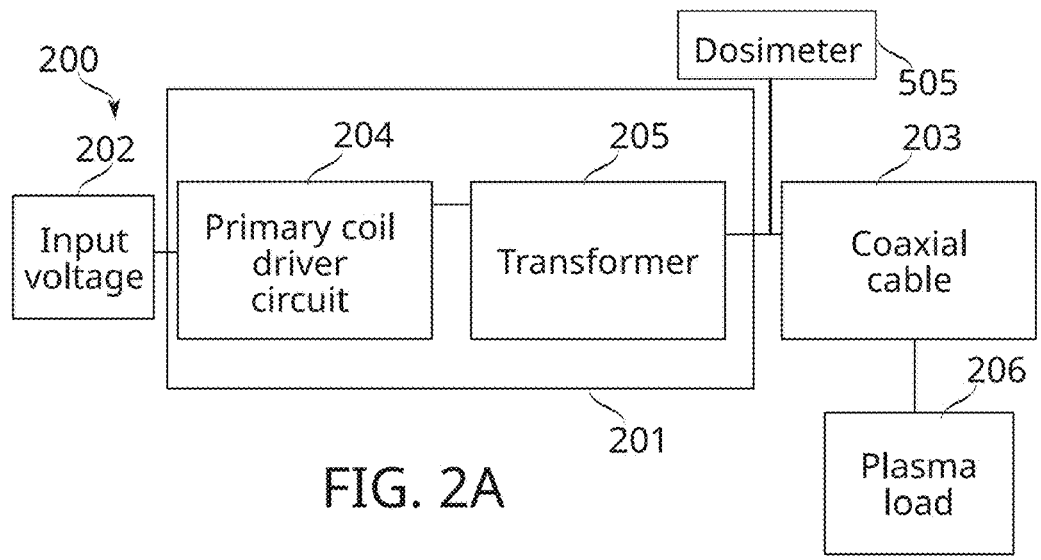
FIGS. 2A-2B schematically represent an intra-body plasma application system, illustrating a potential problem for design of a plasma generation system, addressed in some embodiments of the present disclosure.
Figure 2B:
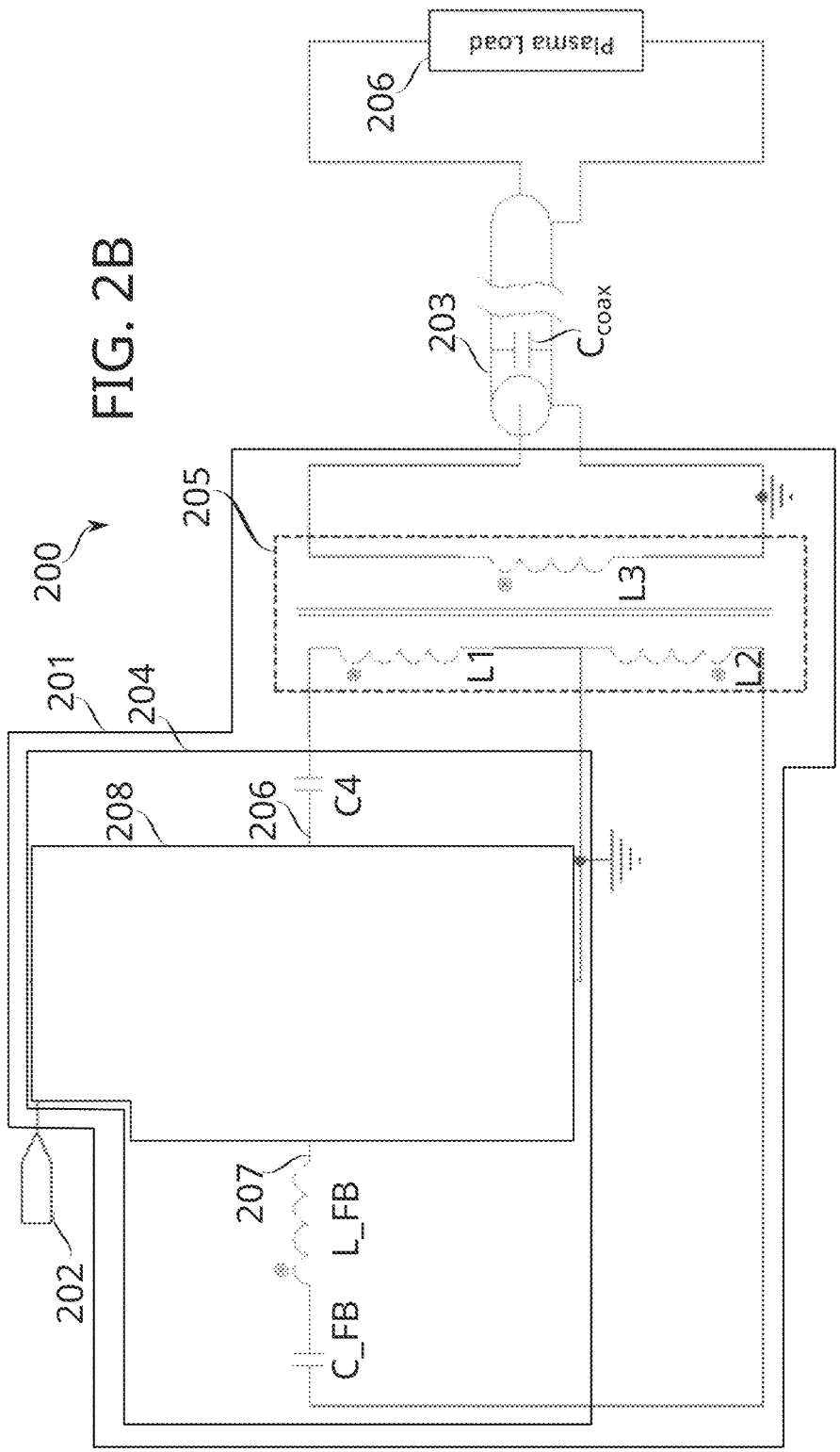

Reference is now made to FIGS. 2A-2B, which schematically represent an intra-body plasma application system 200, illustrating a potential problem for design of a plasma generation system, addressed in some embodiments of the present disclosure. FIG. 2A is a schematic block diagram of system 200, while FIG. 2B represents a component-level implementation of the schematic block diagram of FIG. 2A.

In the example shown, generator 201 and coaxial cable 203 operate together to generate a high-voltage driving signal for the plasma gun. Generator 201 comprises a primary coil driver circuit 204 comprising amplifier 208, activated by input voltage 202, and driving the primary coil of transformer 205. Coaxial cable 203, in some embodiments, comprises a flexible electrical transmission line interconnected with the secondary coil of transformer 205, so as to conduct a high voltage to a plasma generating site near its terminal end, whereat plasma is generated which constitutes the plasma load 206.

To generate plasma, an ionizing gas is also conducted to the plasma generating site, optionally through a conduit which extends alongside coaxial cable 203 to reach the plasma generating site. In some embodiments, the coaxial cable 203 is inserted within a body to be treated (e.g., inserted along the lumen of a body cavity) while the high voltage delivered, along with ionizing gas, to generate plasma. The voltage high-frequency alternating; e.g., at a frequency of several kilohertz, for example, 100 kHz or higher. It is noted that dosimetry of the plasma produced is optionally achieved by one or more of several arrangements and/or methods. For example, the signal (e.g., its power, frequency, and/or waveform) used to generate plasma may be monitored by dosimetry circuitry (e.g., circuitry in communication with optional dosimeter 505) arranged to make measurements of the signal just before it enters coaxial cable 203, and/or at another location in circuitry the overall system. Optionally, the plasma itself is monitored, e.g., optically or electrically, by sensors near to the site of plasma generation (plasma load 206), communicating with dosimeter 505.

The implementation of FIG. 2B indicates the capacitance $C_{coax}$ of coaxial cable 203, which, in some embodiments, adds significant capacitance to the overall load driven by generator 201 via primary coil driver circuit 204. This capacitance is a general property to be expected of any type of transmission line.

With increasing targeted frequency of operation, this added capacitance eventually becomes limiting on the bandwidth that generator 201 can achieve for a given voltage amplitude. At relatively low frequencies of several kHz, the added capacitance $C_{coax}$ is insignificant for realistic cable lengths of 2-3 m.

However, to increase the frequency into the MHz range, it is a potential advantage to use a resonating generator configuration, such as is shown in FIG. 2B. The resonating generator relies on the cable capacitance to form (along with transformer 205) an 'LC'-type resonator circuit which can be tailored to a specific resonance frequency. This generated frequency, along with the high voltage provided from the transformer high-side (the secondary coil of the transformer), are fed directly to the plasma generating portion.

It should be noted that this power signal generation approach is distinct in character from an approach which generates a power signal of a frequency which is merely selected to match the time constant of the load. The matching in that case is needed for efficient transmission of a signal already generated. Integration of the load and its electrical characteristics into the generator circuit itself has potential disadvantages for flexibility of power generation parameters. For example, frequency selection adjustment in a standard power supply should match load impedance to get efficient transmission into the load, but the frequency of the power supply signal itself may be selectable relatively freely without preventing its generation. When the load becomes part of the signal generating circuit, adjustment of frequency outside of a limited range means adjusting electrical characteristics of the load and driver circuits in concert. If adjustment is not concerted, the signal generating circuit may simply cease to generate a signal at all.

In some embodiments of the present disclosure, matching performs a function over and above achieving efficient transmission of a power signal; it also affects generation of the power signal itself. The frequency of that power signal is intrinsically (that is, as a matter of proximate cause, not just as a matter of predetermined selection) generated as a function of the load characteristics. Change the load, and the frequency changes too. This is not to say that the power supply will generate efficiently at any frequency selected by the resonance of the LC circuit comprising $C_{coax}$ and L3; it must operate within its own limits. Change the load characteristics too much, and power signal generation itself is impaired. In the entire absence of load-side resonance, power signal generation stops, due to extreme network mismatch.

In effect, the transmission line capacitance acts as a key component of the timing signal providing portion of the power signal generator, in such a fashion that either the transmission line inherently can accept the frequency of the power signal being generated (having generated the frequency, it can also accept it)—or else, there is no effective power signal to accept. In effect, the load side of the circuit entrains the oscillation of the driver circuit, in distinction to merely being selected to match its oscillating frequency.

Restated briefly, the capacitance $C_{coax}$ together with the secondary coil inductance L3 are used as primary parameters determining the time constant with which not only they, but also the driving circuit 204 on the primary side of coil 205 oscillate. However, at a sufficiently high frequency, this theoretical circuit becomes practically difficult to realize; for example, because the voltage gain requirements force the selection of an unrealistically low inductance onto the primary coil (comprising inductors L1, L2) of transformer 205.

In the simplified electrical schematic of FIG. 2B, primary coil driver circuit 204 is fed by an input voltage source 202, e.g., a DC voltage measuring up to 100 V. A transformer unit 205 is connected between driver circuit 204 and the transmission line (coaxial cable 203). It comprises 3 coupled inductors: primary coil L1, feedback coil L2 and secondary coil L3.

Amplifier 208 output 206 is connected via decoupling capacitor C4 to the primary coil L1, while the feedback to amplifier 208 at opposing polarity is connected via compensation network C_FB and L_FB to the input 207. Matching the time constant of the LC network comprising L3 and $C_{coax}$ by the feedback network comprising L2, L_FB and C_FB results in sinusoidal resonance at a frequency of:

$$f = \frac{1}{2\pi\sqrt{L_3 \cdot C_{coax}}}$$

Considering a typical use-case, there may be, for example, a 2 MHz resonance targeted. A typical capacitance of 2 m of coaxial cable may be, for example, about 200 pF. With these as givens, the secondary coil inductance may be selected to measure 31 µH.

In some embodiments, capacitance of the transmission line (the transmission line comprising e.g., coaxial cable, twisted pair cable, or another conductor configuration) is at least 50 pF, 100 pF, 150 pF, or 200 pF. In some embodiments, the length of the transmission line is at least 50 cm, 100 cm, 150 cm, 200 cm. Secondary could inductance is selected accordingly.

As a further design parameter, a modest working high-voltage of 1 kV RMS may be assigned at the plasma load 206, but higher working voltages may be desired, for example, at least 1.5 kV RMS or at least 2 kV RMS.

For reasonable input voltages the transformer 205 will have a gain ratio in the range of about 30-50. Insofar as the gain ratio is in proportion to the square root of the inductance ratio, this places a constraint on the primary coil inductance to be in the range of approximately 0.01-0.03 µH:

$$\text{Transformer Gain} = \sqrt{\frac{L_{secondary(3)}}{L_{Primary(1)}}}$$

Use of such a low primary-side inductance in a transformer design for use with such high voltages is impractical. Physical constraints ordinarily lead to single coil inductors of a few nH having typical sizes of only a few millimeters (e.g., 4 mm or less) in their largest dimension. A corresponding transformer, even if somehow constructed, would have to handle huge current loads at the target voltages (0.01 µH is equivalent to about 0.1Ω at 2 MHz), resulting in transformer saturation, among other parasitic effects such as the skin effect. There are also concerns with heating and electrical insulation. Increasing input voltage (which allows reducing gain while maintaining the targeted output voltage), significantly decreases generator efficiency (also resulting in heat), and beyond a certain point also becomes impractical.

At more moderate frequencies, constraints relax enough that transformer 205 may be of practical use. For example, for a plasma generator unit driven by 1 kV RMS at 1 MHz into a 100 pF cable, the following driving circuitry can be used: a 100 µH secondary side inductance, a 1 µH primary side inductance (leading to a gain of about 10), and an input voltage of 90 V. The transformer's feedback coil inductance is typically of less importance but ordinarily is about the same as the inductance of the primary side coil.

If, in the above example, the capacitance of coaxial cable 203 is modified so that $C_{coax}$ is 100 pF (other components remaining equal), there is expected to be a resulting sharp rise of frequency, reduction in efficiency, and potentially even complete loss of resonance if further decrease in capacitance is performed. Similarly, increasing the cable capacitance (e.g., by increasing its length) will result in decreased frequency and loss of efficiency. In either case, the loss in efficiency is due to the introduction of a mismatch between the feedback (C_FB, L_FB and L2) LC network and the primary (L3 and $C_{coax}$) LC network.

High-Voltage Generator with Dual-Transformer Stages

Figure 3A:
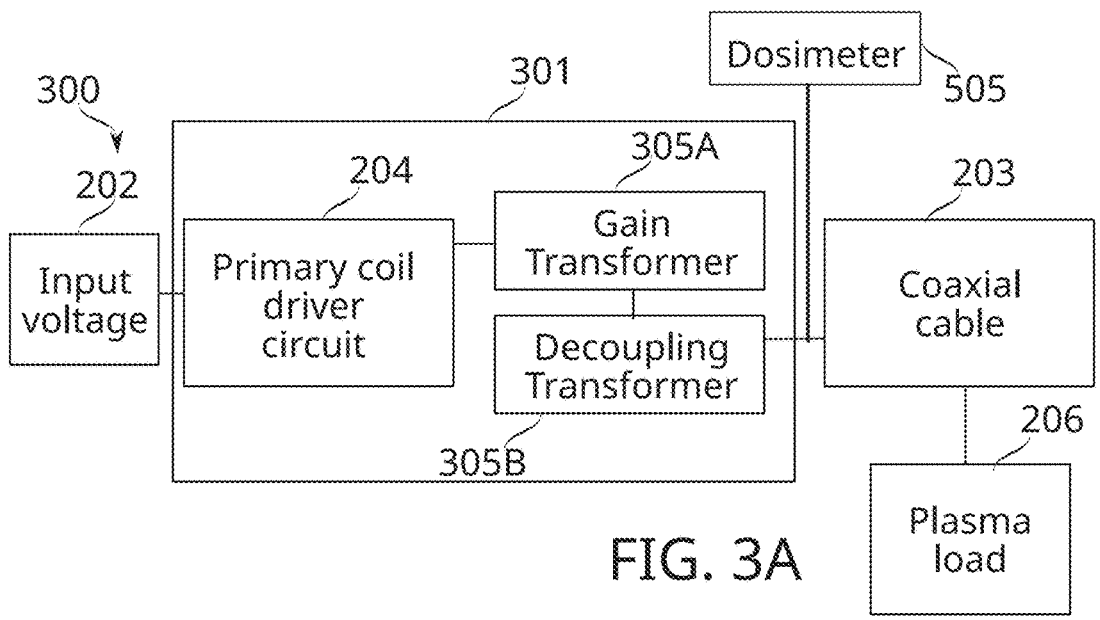
FIG. 3A schematically illustrates a block diagram of a resonating high-voltage plasma generating system, according to some embodiments of the present disclosure.
Figure 3B:
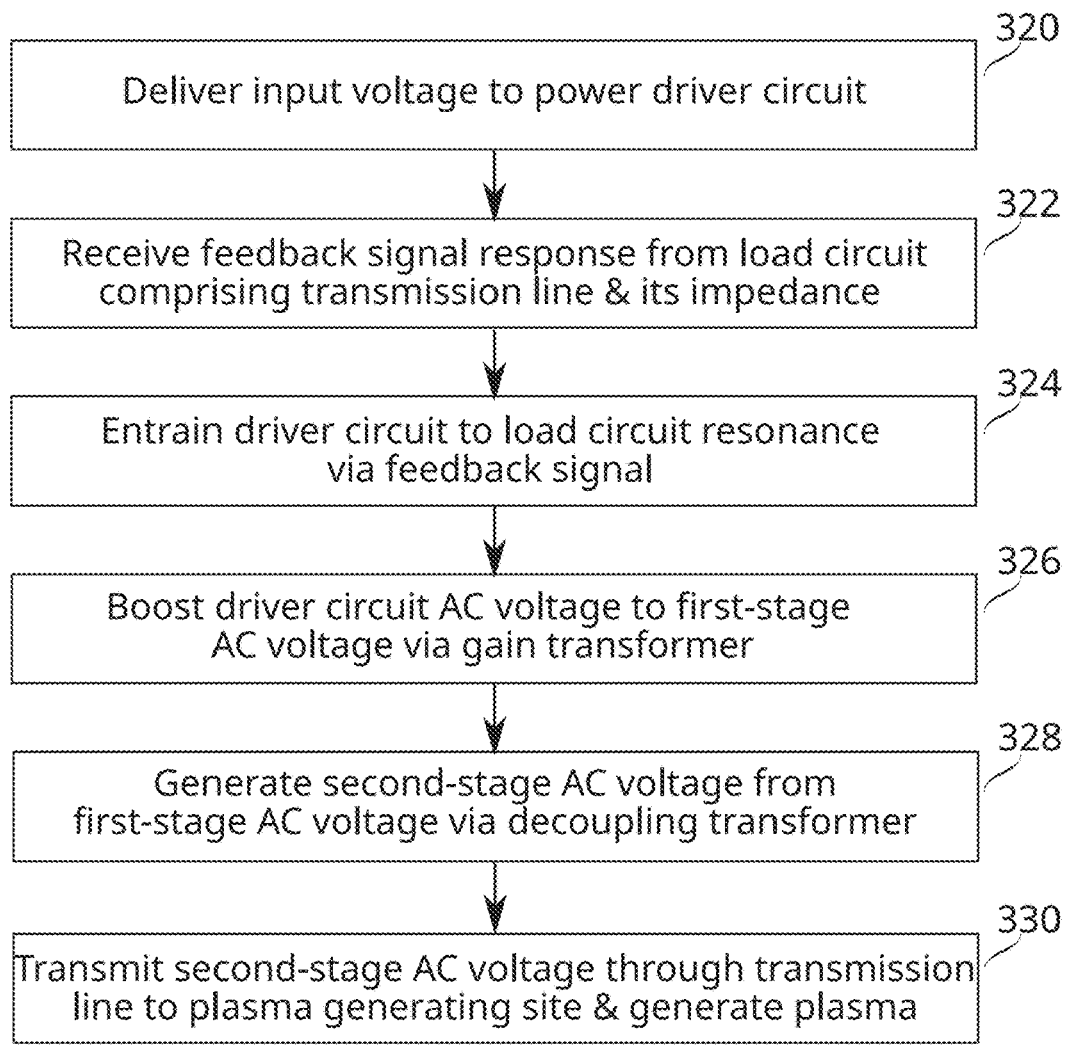
FIG. 3B schematically illustrates a flowchart of a method of operation of a resonating high-voltage plasma generating system, according to some embodiments of the present disclosure.
Figure 3C:
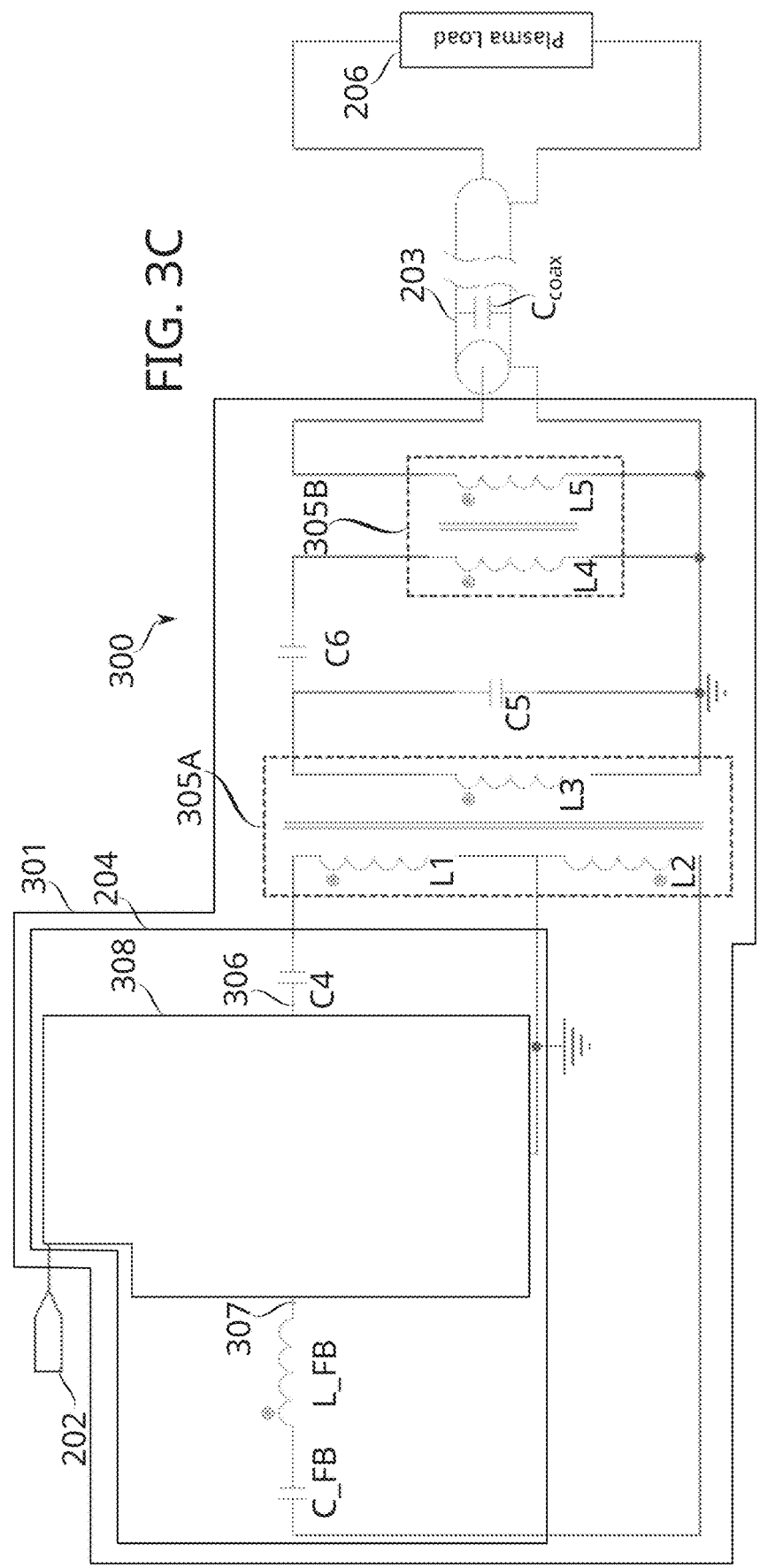
FIG. 3C schematically illustrates a circuit diagram of a resonating high-voltage plasma generating system, according to some embodiments of the present disclosure.
Figure 5A:
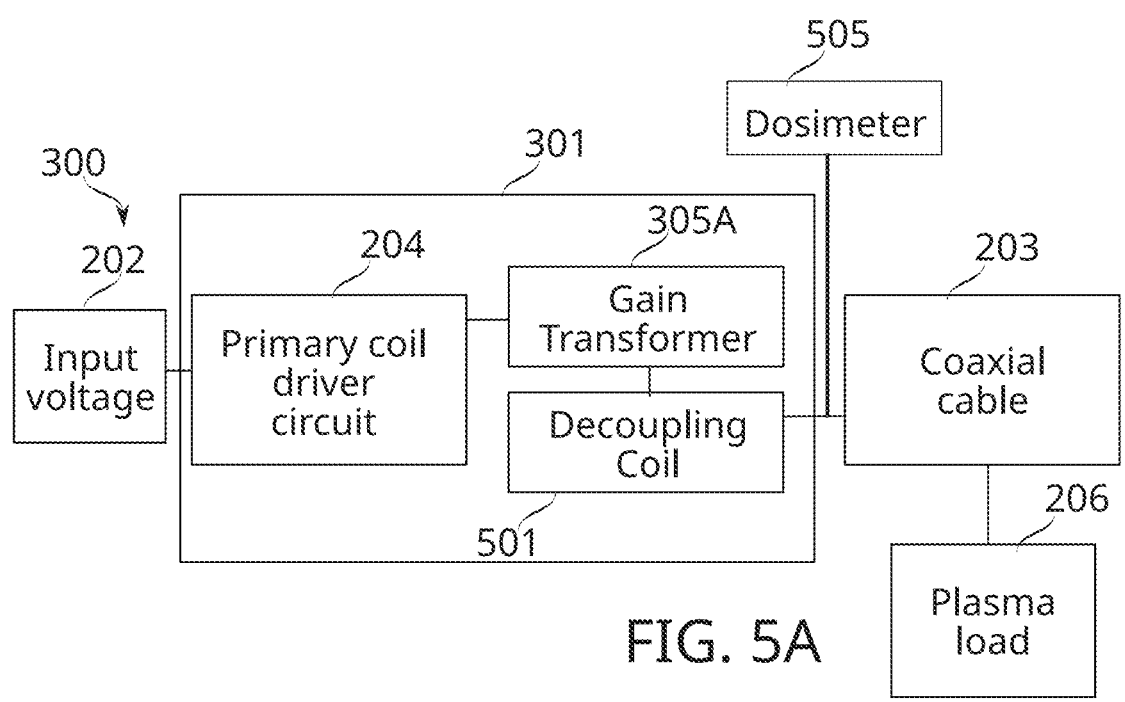
FIGS. 5A-5B schematically illustrate a variation of a resonating high-voltage plasma generating system using a decoupling coil, according to some embodiments of the present disclosure.
Figure 5B:
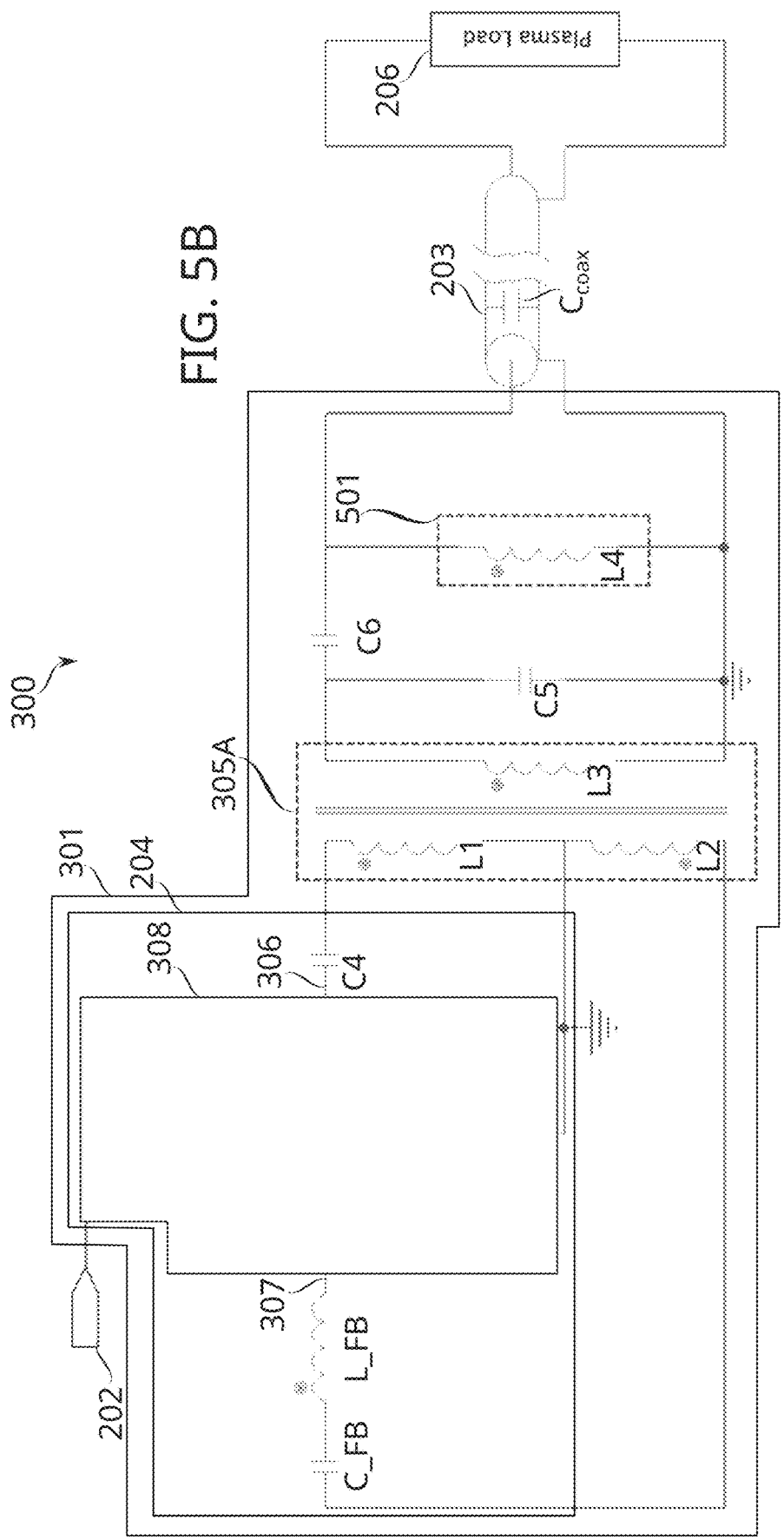

Reference is now made to FIGS. 3A and 3C, which schematically illustrate a resonating high-voltage plasma generating system 300, according to some embodiments of the present disclosure. Reference is also made to FIGS. 5A and 5B, which schematically illustrate a variation of a resonating high-voltage plasma generating system 300 using a decoupling coil 501, according to some embodiments of the present disclosure. Compared to the block diagram of FIG. 2A, generator 301 of FIGS. 3A and 5A divides transformer 205 into a two-stage transformer: a gain transformer 305A, and a decoupling transformer 305B or decoupling coil 501. Descriptions with respect to FIGS. 3A and 3C also apply to the embodiments of FIGS. 5A and 5B, changed as appropriate to accommodate the substitution of decoupling coil 501 for decoupling transformer 305B. This substitution is related to further hereinbelow.

In some embodiments, this allows driving a relatively high-capacitance load while retaining potential advantages of a resonating architecture to achieve a high frequency and potentially true sinusoidal output while generating plasma.

Considering driver circuit 204 (comprising amplifier 308, output 306, and feedback input 307) in combination with gain transformer 305A, basic resonance is achieved by matching the time constant of the L3 and C5 LC network with the feedback LC network comprising (C_FB, L_FB, and L2). C5 can be selected as a small value (e.g., within a factor of ten of 1-5 pF). This allows the corresponding secondary coil inductance L3 to be substantially higher. This also allows the primary and/or feedback coil inductances (e.g., L1 and/or L2) to be substantially higher, potentially entering into a practical range that allows a gain which was otherwise not available at frequencies of, for example, 1-2 MHz. In some embodiments, primary coil L1 has an inductance in the range of about 1-5 µH, secondary coil L3 has an inductance in the range of about 1000-5000 µH, and feedback coil L2 has an inductance in the range of about 0.1-10 µH.

The remainder of the circuit delivers the high frequency, high voltages signal to the load. Capacitor C6 decouples the generated signal. It may measure, for example, within a range from several tenths of a nanoFarad up to hundreds of nF (e.g., in a range of 0.1-900 nF; for example, 0.5-2 nF, 2-10 nF, 0.1-10 nF, 5-20 nF, 20-100 nF, 50-500 nF, or another capacitance range). Relatively lower capacitances have the potential advantage of increasing the rates of system response, for example in aspects such as oscillation frequency and rate of voltage stabilization (meaning-voltage reaches its driven values sooner, since there is less capacitance being charged). Relatively higher capacitances have the potential advantage of reducing general instability characteristics, such as a tendency to overshoot the intended voltage, and potentially to not always reach the same voltage (e.g., instability cycle-to-cycle, and/or unstable mode of operation).

Beyond it, an additional decoupling transformer 305B is used, having a primary side inductance L4 and secondary side inductance L5. Optionally, this transformer is configured to unity gain (L4=L5, optionally chosen to a value within about a factor of ten of 100 µH, for example, a value within the range of 20-200 µH). Alternatively, this transformer is used as a second stage gain. For example, by setting L4 to a value in the range of about 5-20 µH and L5 to a value in the range of about 20-80 µH; e.g., such that an effective second stage gain of 1-4 (for example, 2) is achieved. Finally, the LC network comprising L5 and $C_{coax}$ is designed to match the resonance frequency set by the driver circuit 204 and the gain transformer.

Dosimetry is optionally performed using optional dosimeter 505; for example, using one or more of the implementations described in relation to FIG. 2A.

In some embodiments, the role of decoupling transformer 305B (FIGS. 3A and 3C) is performed by a single decoupling coil 501 (FIGS. 5A and 5B), connected in electrical parallel with the plasma load 206. It may be understood that in embodiments wherein a decoupling transformer 305B provides unity gain, there is a potential loss of ideal behavior insofar as coupling between the primary side and secondary side is non-ideal. This potentially includes efficiency losses. However, decoupling coil 501 is used, in some embodiments, as a substituted equivalent to a unity gain decoupling transformer 305B; i.e., equivalent insofar as the function of providing inductance which affects the circuit's resonant frequency is concerned. This substitution provides the potential advantage of avoiding transformer losses, while maintaining certain of the potential advantages described in the following discussion (i.e., those which do not rely on having a gain other than one).

The embodiments of the two pairs of figures (FIGS. 3A and 3C as one pair, and FIGS. 5A and 5B as the other pair) may be characterized in common as providing decoupling of the impedance of the plasma probe from the impedance characteristics of the gain transformer. More particularly, they decouple the constraints of probe lead capacitance (coaxial cable capacitance) from constraints of gain transformer design which affect characteristics such as the operating voltage, carrier frequency, and/or efficiency of the system. They may be characterized in common as each including an inductance connected between the conductors of coaxial cable 203 and/or in parallel with plasma load 206; and as including an inductance connected in parallel with a secondary coil of transform 305A (having secondary coil inductance L3) and/or in parallel with capacitance C5. In the case of the embodiments of FIGS. 5A-5B, each such defined "inductance connected in parallel" is embodied in the same inductance provided by the same inductive component (e.g., an inductor coil), while in the case of the embodiments of FIGS. 3A and 3C, there are two separately provided inductive components (e.g., two inductor coils of a transformer). Accordingly, there is provided in either case at least one decoupling inductor, providing inductance including inductance connected in parallel to the secondary coil, and inductance connected in parallel to the plasma generating site.

While it is potentially convenient to provide each inductive component as a single inductive coil, there is no inherent obstacle to providing the inductive components in other configurations of inductive sub-components arranged in electrical series and/or electrical parallel as may be suitable to provide a targeted effective inductance influencing the rest of the circuit. Nor is there a particular impediment to partial sharing and partial separation of the separately defined inductances, which is optionally provided in some embodiments of the present disclosure. In some embodiments, some non-shared portion of the differently defined inductances may optionally be provided in the form of a transformer having a non-unity gain.

There are some electrical differences due to the substitution; however, these may be reasonably understood as not impairing or distorting the essential function of the circuit. For example, it may be noted that in FIG. 3C, only one side of each of the coils providing inductances L4, L1 is conductively connected, while the embodiment using decoupling coil 501 is, effectively, conductively connected on both sides. However, the use of unity gain means that there is (again, ideally) no voltage potential difference on either side of the coils in any case, so that conductively interconnecting them does not affect their behavior. Differences in voltage and/or phase which may occur in the non-ideal case for embodiments using a decoupling transformer 305B are not particularly relied on or essential to device function.

There may also be differences in single coil current carried. Optionally decoupling coil 501 is designed (e.g., with a heavier conductor) to withstand higher currents (e.g., 2x higher) than either of the individual coils of decoupling transformer 305B carries alone.

At least three substantial potential advantages are identifiable which may achieved by one or more of these configurations compared to traditional resonant transformer configuration.

First, coupling between frequency and gain is loosened by adding an additional design degree of freedom. In the design of FIGS. 2A-2B:

$$f = \frac{1}{2\pi \cdot \text{Gain} \cdot \sqrt{L_1} \cdot \sqrt{C_{coax}}} = \frac{K}{\text{Gain} \cdot \sqrt{L_1}}$$

Where the capacitance $C_{coax}$ ends up being absorbed into the design requirement-fixed constant K, insofar as it is constrained to be a relatively large value. This yields the already described inverse relationship between frequency f and the inductance L1 and the design gain. Increasing the frequency requires reducing either or both of L1 and the gain to levels with potentially impractical consequences for construction and/or operation of the device.

Using a second transformer stage introduces the option to use C5 as a compensation capacitor (an additional degree of design freedom):

$$f = \frac{1}{2\pi \cdot \text{Gain} \cdot \sqrt{L_1} \cdot \sqrt{C_{coax}} \cdot \sqrt{C_5}} = \frac{K}{\text{Gain} \cdot \sqrt{L_1} \cdot \sqrt{L_5}}$$

Second, limitations on coaxial cable length are relaxed. As just mentioned, $C_{coax}$ may be considered as having a lower limit imposed by design requirements to have a long, thin, flexible cable to allow reaching remote targets to which plasma is applied. It is a potential advantage, in some embodiments of the present disclosure, to lengthen coaxial cable 203 beyond the length that results in this lower limit. The introduction of C5 as a design degree of freedom also allows this. While the minimum practical value of transformer inductance L5 remains a limitation for any given selected target resonant frequency f, it can still be much smaller in the decoupling transformer 305B than in a gain transformer 305A, since a requirement that the primary inductance L4 be much smaller still has been removed.

Third, variation in frequency due to changes in load impedance may be reduced, at least if the second stage gain is selected to be greater than one. Impedance could change, for example, a result damage. It is a potential advantage to reduce sensitivity to minor fluctuations, while still retaining the auto-attenuating effects of large impedance changes. Even for a fixed load impedance, manufacturing tolerances of several percent (e.g., 10%) may apply to key electrical properties of components, potentially including the capacitance of a transmission line. It is a potential advantage to reduce sensitivity of a resonance driver circuit to variation in, e.g., transmission line capacitance, while also retaining advantages of a resonance circuit, for example self-stopping of high frequency signal generation should the transmission line become disconnected.

In a single-stage resonant generator, the capacitance of the transmission line directly relates to frequency as $f \propto (C_{coax})^{-0.5}$. Adding a second stage adds significant complexity to this relation. The transmission line and second stage together may be "seen" as an equivalent capacitance, as far as effect on frequency are concerned, such that $f \propto (C_{equiv})^{-0.5}$. A theoretical dependence of $C_{equiv}$ on $C_{coax}$ may then in turn be expressed as $$C_{equiv} \propto \frac{C_{coax}}{M^2},$$

where the effective gain of the second stage is M.

From this, it may be understood that setting a gain M>1 reduces variation in oscillation frequency due to (absolute) changes in load impedance. For simplicity, ohmic components present in a practical system were omitted in the above relation (e.g., electrical series resistance). Considering these, sensitivity to load impedance may increase somewhat.

Figure 3D:
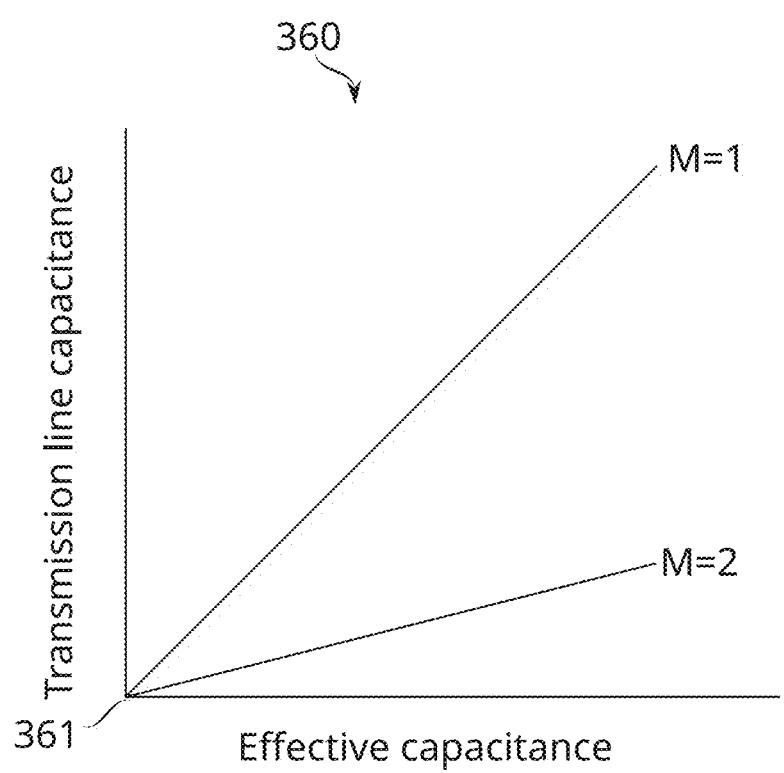
FIG. 3D schematically represents reduction in the theoretical dependence of $C_{equiv}$ on $C_{coax}$ at gain levels M=1 and M=2; according to some embodiments of the present disclosure.

Brief reference is now made to FIG. 3D, which schematically represents reduction in the theoretical dependence of $C_{equiv}$ on $C_{coax}$ at gain levels M=1 and M=2. At the origin 361 is a zero transmission line capacitance; the effective capacitance is a baseline value, not necessarily zero.

With increasing gain M, dependency of effective capacitance on transmission line capacitance reduces. Details of this relationship will vary in practical circuits, e.g., according to the presence of other impedances such as parasitic impedances.

In system 300, if the coaxial cable 203 is disconnected from the circuit, there remains a resonance circuit on the primary side of the decoupling transformer. However, disconnection will also change how the decoupling transformer contributes to that resonance circuit, leading in any case to a likely loss of high-frequency power generation.

When the coaxial cable 203 is re-attached, the effective resonance of the two sides of the decoupling transformer together is still part of the load side of the circuit. This is true in the functional sense that if the circuits on either side of the decoupling transformer don't allow resonance at a mutually compatible frequency, they can't provide the needed frequency that allows the driver circuit 204 to perform its switching. The true (power dissipating) load circuit is still acting to instruct the driver circuit, albeit through and in co-operation with the circuit driving the primary inductance of the decoupling transformer.

As noted above, that influence can diminish with increasing gain on the decoupling transformer. However, even in embodiments where a gain higher than one is used, the effect of an impedance mismatch (e.g., due to damage to the coaxial cable 203) is characteristic. If the effect on the resonance of the primary side of the decoupling transformer manages (despite the gain) to be large enough, it leads to the same failure mode as before: loss of load resonance amplitude, loss of driver circuit entrainment, and ultimately reduction of power or potentially failure to generate power. To the extent that the impedance mismatch is not large enough to seriously reduce resonance of the primary side of the decoupling transform, then the problem is halted too: the driver circuit 204 does not see it. The state of the load circuit remains a failsafe.

Reference is now made to FIG. 3B, which schematically represents a flowchart of a method of operation of a resonating high-voltage plasma generating system according to some embodiments of the present disclosure.

At block 320, in some embodiments, input voltage 202 is delivered to a power driver circuit (e.g., comprising block 204 of FIG. 3A).

FIG. 3B presents the operations of blocks 322-330 are presented in an order (e.g., indicated by the arrows) suitable for descriptive purposes of their mutual dependencies; however it should be understood that operations in an actual device are casually interrelated such that they may all develop simultaneously and/or at least partially in reaction to each other, as aspects of the operation of the circuitry as a whole. For example, the feedback signal mentioned at block 322 is itself established, in some embodiments, as a result of electrical field interactions occurring at the gain transformer, and mentioned in block 326, which in turn are affected by the generation (block 328) and transmission (block 330) of second-stage AC voltages. Effects of the operations of block 330 may be considered, accordingly, as leading back upon the operations of block 322, in the sense of indicating mutual dependency of occurrences in the circuit. Thus, one may have a condition wherein without the feedback of block 322 there is no AC voltage generated and transmitted at blocks 328, 330, but also it may be said that without that AC voltage, there is no feedback.

At block 322, in some embodiments, and via at least gain transformer 305A, a feedback signal generated in response to activation in turn by the power driver circuit is received from a load circuit comprising at least a transmission line (e.g., coaxial cable 203).

At block 324, in some embodiments, the feedback signal entrains the driver circuit to oscillate, the oscillation being tuned (through the feedback signal) to the resonant frequency of the load circuit.

At block 326, in some embodiments, an AC voltage generated by the entrained driver circuit is boosted to a higher voltage by inductive coupling at a gain transformer 305A. The higher voltage is present on the secondary (output) side of the gain transformer 305A in a first stage of the load-circuit side of the overall power generating circuit.

At block 328, in some embodiments, the AC voltage on the first-stage (primary/input) side of decoupling transformer 305B induces a voltage on the second-stage (secondary/output) side of decoupling transformer 305B. In some embodiments, gain at decoupling transformer 305B is equal to or lower than the gain on the gain transform 305A. Optionally gain at decoupling transformer 305B is about 1 (e.g. no gain). Optionally, decoupling transformer 305B is replaced by a decoupling coil 501 or another configuration of decoupling inductances; for example as described in relation to FIGS. 5A-5B. Optionally, the gain of gain transformer 305A is smaller than gain at gain transformer 305B by a factor of at least 1.5, 2, 3, 4, 5 or more.

At block 330, in some embodiments, the second-stage voltage is transmitted along a transmission line (e.g., coaxial cable 203 or a cable of another design, for example, twisted pair), reaches a plasma generating site, and provides power used to generate plasma.

High-Voltage Generator with Multiple-Transformer Stages

Figure 4A:
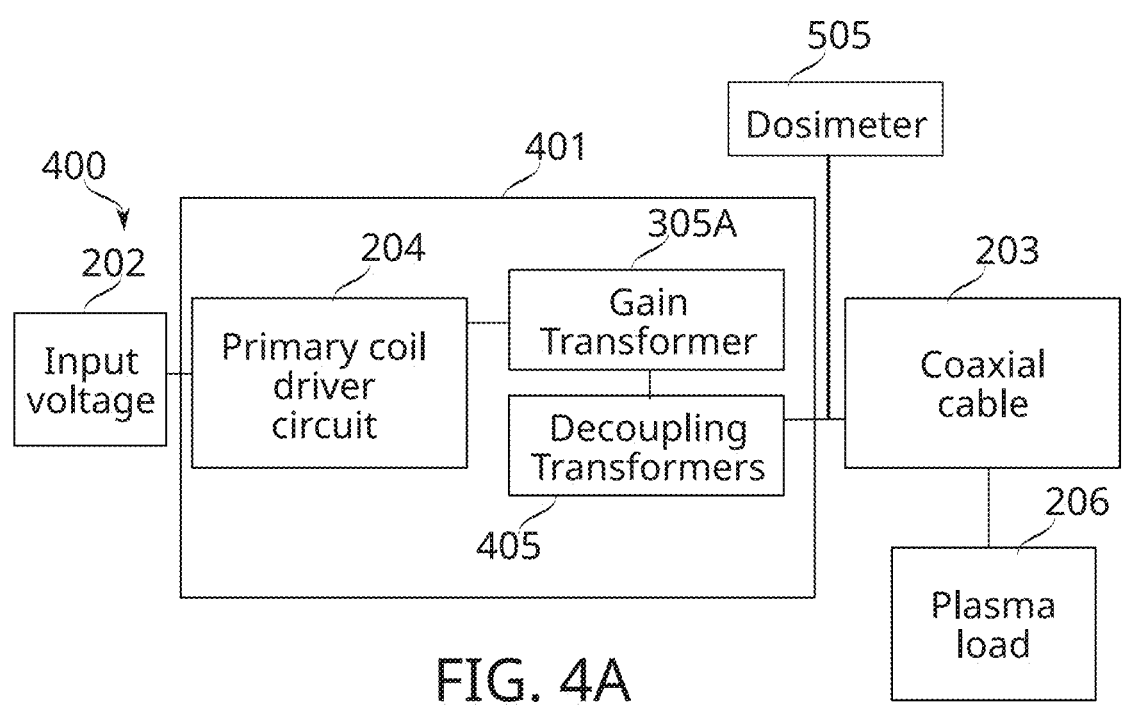

Reference is now made to FIGS. 4A-4B, which schematically illustrate a resonating high-voltage plasma generating system 400, according to some embodiments of the present disclosure. Compared to the block diagram of FIG. 3A, generator 401 of FIG. 4A divides decoupling transformer 305B into a plurality of n decoupling transformers 405 where n≥2. The plurality of decoupling transformers are represented in FIG. 4B as sub-stages 405B, 405C, and 405D, driven from driver circuit 204 (which comprises amplifier 308 having feedback input 307 and output 306). Not all components are shown for sub-stages beyond 405B, but they may be understood as repeating the unit of sub-stage 405B with the connectivity shown. Sub-stage 405C may be understood as representing one or more "intermediate" sub-stages. Dosimetry is optionally performed using optional dosimeter 505; for example, using one or more of the implementations described in relation to FIG. 2A.

Division of the decoupling transformer 305B into a plurality of decoupling transformers 405 generalizes on the dual-transformer architecture of FIGS. 3A and 3C. Although more complex, the multiple stage design has the potential advantage of distributing voltage gain, if such is required, beyond what may be practical in a two transformer design while maintaining a high operating (resonant) frequency.

Another potential advantage is reduced sensitivity to variations of the load impedance, generalizing to:

$$C_{equiv.} \propto \frac{C_{coax}}{M_1^2 M_2^2 \ldots M_n^2} = \frac{C_{coax}}{\prod_1^n M_n^2}$$

Where: $M_n$ is the gain of the $n^{th}$ transformer stage. Impedance matching is preferably still attended to, however, to prevent signal reflections and harmonic distortions. It should be understood that each additional stage reduces overall efficiency, particularly in practical systems including resistive losses and parasitic capacitances.

The method of FIG. 3B also applies, in some embodiments, to the operation of the device of FIGS. 4A-4B, changed as necessary to account for additional stages. For example, it applies with the modification that the operations of block 328 are duplicated as necessary among a plurality of decoupling stages until the last decoupling stage is reached, at which said last stage transmission of the final AC voltage occurs through the transmission line to the plasma generating site to generate plasma.

In some embodiments, the transmission line (cable 203) itself is part of one or more of the intermediate stages, with one or more decoupling transformers located along the transmission line. This includes the option of dividing cable 203 into inductively coupled segments.

General

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the present disclosure may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments may be presented with reference to a range format. It should be understood that the description in range format is merely for convenience and brevity and should not be construed as an inflexible limitation on the scope of descriptions of the present disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although descriptions of the present disclosure are provided in conjunction with specific embodiments, it is evident that many alternatives, modifications and variations will be apparent to those skilled in the art. Accordingly, it is intended to embrace all such alternatives, modifications and variations that fall within the spirit and broad scope of the appended claims.

It is appreciated that certain features which are, for clarity, described in the present disclosure in the context of separate embodiments, may also be provided in combination in a single embodiment. Conversely, various features, which are, for brevity, described in the context of a single embodiment, may also be provided separately or in any suitable subcombination or as suitable in any other described embodiment of the present disclosure. Certain features described in the context of various embodiments are not to be considered essential features of those embodiments, unless the embodiment is inoperative without those elements.

It is the intent of the applicant(s) that all publications, patents and patent applications referred to in this specification are to be incorporated in their entirety by reference into the specification, to the same extent as if each individual publication, patent or patent application was specifically and individually noted when referenced that it is to be incorporated herein by reference. In addition, citation or identification of any reference in this application shall not be construed as an admission that such reference is available as prior art to the present disclosure. To the extent that section headings are used, they should not be construed as necessarily limiting. In addition, any priority document(s) of this application is/are hereby incorporated herein by reference in its/their entirety.

What is claimed is:

1. A non-thermal plasma generator comprising:
   a gain transformer comprising a primary coil and a secondary coil;
   a driver circuit electrically connected to drive a current through the primary coil;
   a load circuit having a distal end comprising a plasma generating site generating non-thermal plasma, and a proximal end coupled to the secondary coil of the gain transformer;
   wherein the load circuit comprises at least one decoupling inductor, providing inductance including inductance connected in parallel to the secondary coil, and inductance connected in parallel to the plasma generating site.

2. The non-thermal plasma generator of claim 1, wherein the load circuit has an impedance determining a frequency of oscillation of the load circuit in response to a current generated in the secondary coil.

3. The non-thermal plasma generator of claim 2, wherein the load circuit entrains oscillation of the driver circuit.

4. The non-thermal plasma generator of claim 3, wherein oscillation of the driver circuit is entrained via feedback from the gain transformer.

5. The non-thermal plasma generator of claim 4, wherein the feedback from the gain transformer is provided by a feedback winding of the gain transformer, and wherein the feedback winding has an inductance in the range of about 1-10 µH.

6. The non-thermal plasma generator of claim 2, wherein the frequency of oscillation of the load circuit is sufficiently high that plasma generation at the plasma generating site does not extinguish during at least a full oscillation cycle.

7. The non-thermal plasma generator of claim 2, comprising pulse modulation circuitry operable to modulate the frequency of oscillation at a lower frequency within the range of 0.1-1 KHz.

8. The non-thermal plasma generator of claim 2, wherein the driver circuit ceases oscillation when the plasma generating site is disconnected from the load circuit, but maintains oscillation for values of the frequency of oscillation of the load circuit varying within a range having at least a 10% difference between minimum and maximum values of the range.

9. The non-thermal plasma generator of claim 1, wherein the gain transformer provides a gain of at least 20.

10. The non-thermal plasma generator of claim 9, wherein the at least one decoupling inductor comprises at least one decoupling transformer, providing in aggregate a gain no larger than 1.

11. The non-thermal plasma generator of claim 1, wherein the at least one decoupling inductor comprises decoupling transformers providing in aggregate a gain smaller than the gain provided by the gain transformer by a factor of at least 2.

12. The non-thermal plasma generator of claim 1, wherein the gain transformer comprises air or ferrite core.

13. The non-thermal plasma generator of claim 1, wherein the at least one decoupling inductor comprises a plurality of decoupling transformers.

14. The non-thermal plasma generator of claim 1, wherein the at least one decoupling inductor comprises an inductor coil connected both in parallel to the secondary coil, and in parallel to the plasma generating site.

15. The non-thermal plasma generator of claim 1, wherein an operating voltage amplitude at the plasma generating site produced when the current is driven through the primary coil of the gain transformer is at least 1 kV RMS.

16. The non-thermal plasma generator of claim 1, comprising a transmission line interconnecting the plasma generating site and the at least one decoupling inductor; wherein the transmission line is at least 50 cm long, and flexible.

17. The non-thermal plasma generator of claim 16, provided together with a gas supply lumen leading along the transmission line to the plasma generating site, the gas supply lumen and transmission line together being elements of a flexible probe having an overall diameter of less than 10 mm.

18. The non-thermal plasma generator of claim 15, wherein the at least one decoupling inductor together with the gain transformer comprise a one or more transformers delivering the operating voltage to the plasma generating site with an amplitude at least 20 times larger than a voltage amplitude in the primary coil of the gain transformer.

19. The non-thermal plasma generator of claim 1, wherein the primary coil of the gain transformer has an inductance in the range of about 1-5 µH, and the secondary coil of the gain transformer has an inductance in the range of about 1000-5000 µH.

20. The non-thermal plasma generator of claim 1, wherein the at least one decoupling inductor includes at least one decoupling transformer, and a distal-side coil of the at least one decoupling transformer has an inductance in the range of about 20-80 µH, and is a coil of a distal decoupling transformer of the at least one decoupling transformer having a primary coil with an inductance in the range of about 5-20 µH.

21. The non-thermal plasma generator of claim 1, wherein the at least one decoupling inductor is connected to the plasma generating site through releasable electrical contacts.

* * * * *